(12) United States Patent
Coats et al.

(10) Patent No.: US 11,980,743 B2
(45) Date of Patent: *May 14, 2024

(54) NEEDLE-FREE TRANSDERMAL INJECTION DEVICE

(71) Applicant: Portal Instruments, Inc., Cambridge, MA (US)

(72) Inventors: Andrew Coats, Somerville, MA (US); Robert J. Dyer, Concord, MA (US)

(73) Assignee: Portal Instruments, Inc., Cambridge, MA (US)

( * ) Notice: Subject to any disclaimer, the term of this patent is extended or adjusted under 35 U.S.C. 154(b) by 941 days.

This patent is subject to a terminal disclaimer.

(21) Appl. No.: 16/989,244

(22) Filed: Aug. 10, 2020

(65) Prior Publication Data

US 2020/0368437 A1 Nov. 26, 2020

Related U.S. Application Data

(63) Continuation of application No. 14/952,056, filed on Nov. 25, 2015, now Pat. No. 10,737,032.

(51) Int. Cl.
*A61M 5/30* (2006.01)
*A61M 5/20* (2006.01)

(52) U.S. Cl.
CPC ........ *A61M 5/3007* (2013.01); *A61M 5/2033* (2013.01); *A61M 5/30* (2013.01); *A61M 2205/332* (2013.01); *A61M 2205/3327* (2013.01)

(58) Field of Classification Search
CPC .... A61M 5/3007; A61M 5/30; A61M 5/2033; A61M 2205/50; A61M 2205/3327; A61M 2205/33; A61M 2205/32
See application file for complete search history.

(56) References Cited

U.S. PATENT DOCUMENTS

| | | | |
|---|---|---|---|
| 5,505,697 A | 4/1996 | Mckinnon, Jr. et al. | |
| 6,056,716 A * | 5/2000 | D'Antonio | A61M 5/30 604/134 |
| 6,666,843 B1 | 12/2003 | Alexandre et al. | |
| 6,939,323 B2 | 9/2005 | Angel et al. | |
| 7,833,189 B2 | 11/2010 | Hunter et al. | |
| 8,172,790 B2 * | 5/2012 | Hunter | A61M 5/30 604/68 |

(Continued)

FOREIGN PATENT DOCUMENTS

| | | |
|---|---|---|
| CN | 101588829 A | 11/2009 |
| CN | 104470578 A | 3/2015 |

(Continued)

*Primary Examiner* — Brandy S Lee
*Assistant Examiner* — Hong-Van N Trinh
(74) *Attorney, Agent, or Firm* — Strategic Patents, P.C.

(57) ABSTRACT

An apparatus for use in injectate delivery includes an actuator including a linkage, a force generating mechanism mechanically coupled to the linkage, and a controller coupled to the force generating mechanism. The force generating mechanism includes a passive force generator and an active force generator. In operation and on the basis of a control signal, the controller is configured to control the force generating mechanism to provide an input force to the linkage that is a combination of the first force provided by the passive force generator and a second force provided by the active force generator.

16 Claims, 9 Drawing Sheets

(56) References Cited

U.S. PATENT DOCUMENTS

| | | |
|---|---|---|
| 8,398,583 B2 | 3/2013 | Hunter et al. |
| 8,740,838 B2 | 6/2014 | Hemond et al. |
| 8,821,424 B2 | 9/2014 | Alleyne |
| 2004/0094146 A1 | 5/2004 | Schiewe et al. |
| 2011/0097229 A1 | 4/2011 | Cauley, III et al. |
| 2012/0259282 A1 | 10/2012 | Alderete, Jr. et al. |
| 2015/0122338 A1 | 5/2015 | Hunter et al. |
| 2015/0157809 A1 | 6/2015 | Park et al. |
| 2015/0297864 A1 | 10/2015 | Kokish et al. |

FOREIGN PATENT DOCUMENTS

| | | |
|---|---|---|
| JP | 2005-95700 A | 4/2005 |
| JP | 2005-537907 A | 12/2005 |
| JP | 2008-508961 A | 3/2008 |
| JP | 2013-163105 A | 8/2013 |
| WO | 98/17332 A2 | 4/1998 |
| WO | 2004/022138 A2 | 3/2004 |
| WO | 2008/027579 A1 | 3/2008 |
| WO | 2015/066346 A1 | 5/2015 |
| WO | 2015/102987 A1 | 7/2015 |

\* cited by examiner

NEEDLE-FREE TRANSDERMAL INJECTION DEVICE

CROSS REFERENCE TO RELATED APPLICATIONS

This is a CONTINUATION application priority to U.S. application Ser. No. 14/952,056, filed on Nov. 15, 2015, incorporated herein by reference in its entirety.

BACKGROUND

This invention relates to a needle-free transdermal injection device.

The skin of organisms such as humans serves as a protective barrier that, among other functions, prevents pathogens from entering the body and prevents or regulates fluids such as blood and water from exiting the body. In the field of modern medicine, there is often a need to deliver injectates such as drugs through the skin and into the bloodstream of patients. Traditionally, this delivery of liquids into a patient's body is accomplished by insertion of a needle through the patient's skin and into an area inside of the patient's body where the liquid can enter the patient's blood stream.

However, the use of needles to deliver liquids into a patient's body has a number of significant drawbacks such as the pain associated with being pierced by a needle, the fear that many patients have of needles, and the skin damage and associated risk of infection that occurs due to the use of needles.

As a result, needle-free transdermal injection devices have been developed. These devices use a high pressure, narrow jet of injection liquid or powder to penetrate a patient's skin, obviating the need to pierce the patient's skin with a needle.

SUMMARY

In a general aspect, an apparatus for use in injectate delivery includes an actuator including a linkage, a force generating mechanism mechanically coupled to the linkage, and a controller coupled to the force generating mechanism. The force generating mechanism includes a passive force generator and an active force generator. In operation and on the basis of a control signal, the controller is configured to control the force generating mechanism to provide an input force to the linkage that is a combination of the first force provided by the passive force generator and a second force provided by the active force generator.

Aspects may include one or more of the following features.

The controller may be configured to control the input force provided to the linkage, including controlling the second force provided by the active force generator, to cause movement of the actuator at a target velocity. The controller may be configured to indirectly control the second force provided by the active force generator by controlling a torque generated by the active force generator, wherein the torque is proportional to the second force. The controller may be configured to control the input force provided to the linkage such that velocity of the actuator achieves a target velocity profile over an operational cycle of the apparatus. The apparatus may include a displacement sensor for measuring a displacement of the actuator from a reference position, wherein the controller includes an input for receiving a displacement measurement of the actuator from the displacement sensor and is configured to determine an estimate of a velocity of the actuator based on the received displacement measurement.

The controller may be configured to determine the estimate of the velocity of the actuator based on the received displacement measurement and one or more previously received displacement measurements. The active force generator may include an electromagnetic motor. The electromagnetic motor may include an electromagnetic rotary motor. The electromagnetic motor may include an electromagnetic linear motor. The passive force generator may include an energy storage element storing mechanical energy, said energy storage element configured to cause the passive force generator to provide the first force to the linkage.

The energy storage element may be configured to store mechanical energy as compressed air. The energy storage element may include a spring for storing the mechanical energy. The spring may include a helical spring directly coupled to the linkage. The helical spring may be configurable into a rest state wherein the helical spring stores no mechanical energy and into a compressed state wherein the helical spring stores mechanical energy. The helical spring may be configurable into a rest state wherein the helical spring stores no mechanical energy and into an expanded state wherein the helical spring stores mechanical energy. The spring may include a torsion spring directly coupled to the motor and indirectly coupled to the linkage via the motor. The spring may include a torsion spring directly coupled to the linkage. The spring may include a beam spring.

The apparatus may include chamber for holding an injectate, wherein the actuator is disposed within the chamber and is configured to exert a net force, proportional to the input force on the injectate in the chamber via the linkage during operation. The linkage may include a ball screw.

In another general aspect, an apparatus for delivering a fluid held within a chamber to a patient includes an actuator element for exerting a force on the fluid in the chamber during operation, an electromagnetic motor for driving the actuator element, said motor during operation causing the actuator element to apply a first force component on the fluid in the chamber during a fluid transfer cycle, an energy storage element storing mechanical energy (spring, compressed air), said energy storage element for causing the actuator element to apply a second force component on the fluid in the chamber during the fluid transfer cycle, wherein the total force applied by the actuator on the fluid in the chamber during the fluid transfer cycle is the sum of the first and second force components, and a controller for controlling the electromagnetic motor to dynamically vary the first force component throughout the fluid transfer cycle.

Aspects may have one or more of the following advantages.

Among other advantages, aspects may be able to make use of smaller and less expensive motors for driving the actuator element due to the additional force (and, in some examples, associated torque) supplied by the energy storage element.

Aspects may result in smaller injection devices due to the use of smaller motors.

Aspects may require less power to drive the actuator element due to the use of smaller motors.

Aspects may be able to apply a greater peak force to the actuator element due to the combined use of motors and energy storage elements.

Other features and advantages of the invention are apparent from the following description, and from the claims.

DETAILED DESCRIPTION

1 Needle-Free Transdermal Injection Device

Figure 1:
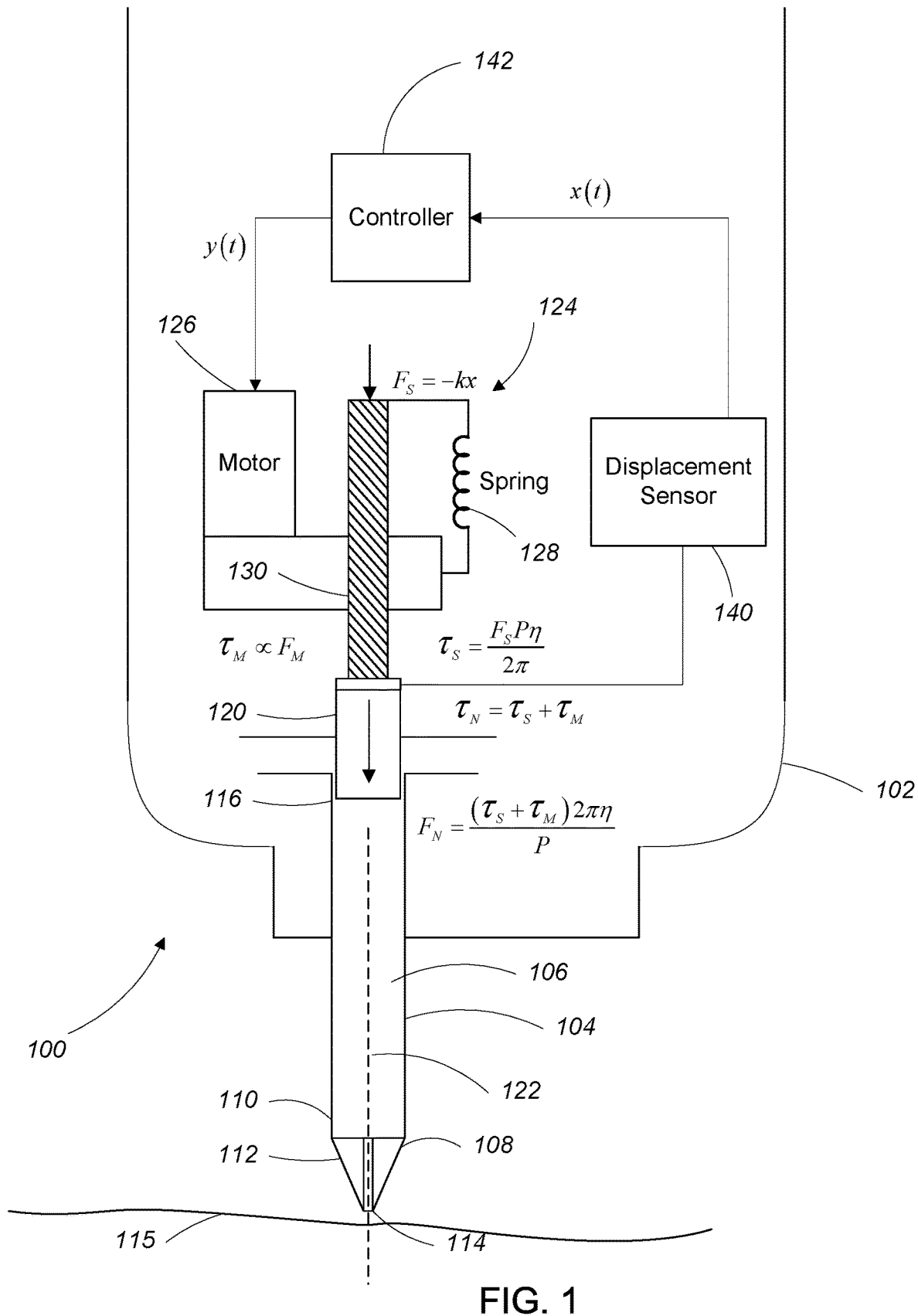
FIG. 1 is a schematic diagram of a controllable, needle-free transdermal injection device.

Referring to FIG. 1, a controllable, needle-free transdermal injection device 100 for transferring an injectate (e.g., a drug or a vaccine in any one of a number of states such as a liquid state or a powder state) through the skin of a patient includes a needle-free transdermal injector head 104 extending from a housing 102. The injector head 104 includes a chamber 106 for holding the injectate and a nozzle 108 disposed at a distal end 110 of the chamber 102. The nozzle 108 includes a head 112 and an opening 114 from which a jet of the injectate is discharged from the chamber 106. In operation, the opening 114 is placed near or against the skin 115 when the injectate is discharged. The dimensions of the nozzle including the inner diameter of opening 114 are an important factor in the transfer (e.g., injection) pressure of the injectate. In some examples, the inner diameter of the opening is in a range of 50 µm to 300 µm. In some examples a length of the nozzle is in a range of 500 µm to 5 mm. In some examples, an outer diameter of the head 112 of the nozzle 108 narrows to the opening 114. In other examples, any one of a number of different nozzle shapes can be used (e.g., the outer diameter of the head 112 of the nozzle 108 may be constant or the head of the nozzle 112 may have a rounded shape).

The chamber 106 has a proximal end 116 and a distal end 110. An actuator (i.e., a piston or plunger 120) is slidably disposed within the chamber 106. Movement of the plunger 120 along a longitudinal axis 122 in either direction can affect the pressure within chamber 106. In some embodiments, the chamber 106 is integral to the device 100. In other embodiments, chamber 106 is separately attachable to device 100.

1.1 Force Generating Mechanism

The injection device 100 includes a force generating mechanism 124 including an actively controlled force generating device 126 (an electromagnetic motor in the embodiment of FIG. 1) and a passive force generating device 128 (a spring in the embodiment of FIG. 1) both of which apply a force to the plunger 120 via a linkage 130 to inject the injectate in chamber 106 through the skin. In some examples, the linkage is a ball screw actuator 130. However, it should be understood that the injection device is not limited to using a ball screw actuator as a linkage. Indeed, many different types of linkages such as lead screws, linear motion bearings, and worm drives can be used instead of a ball screw. In some examples, the choice of linkage is dictated by the cost and weight of the different linkages.

Figure 2:
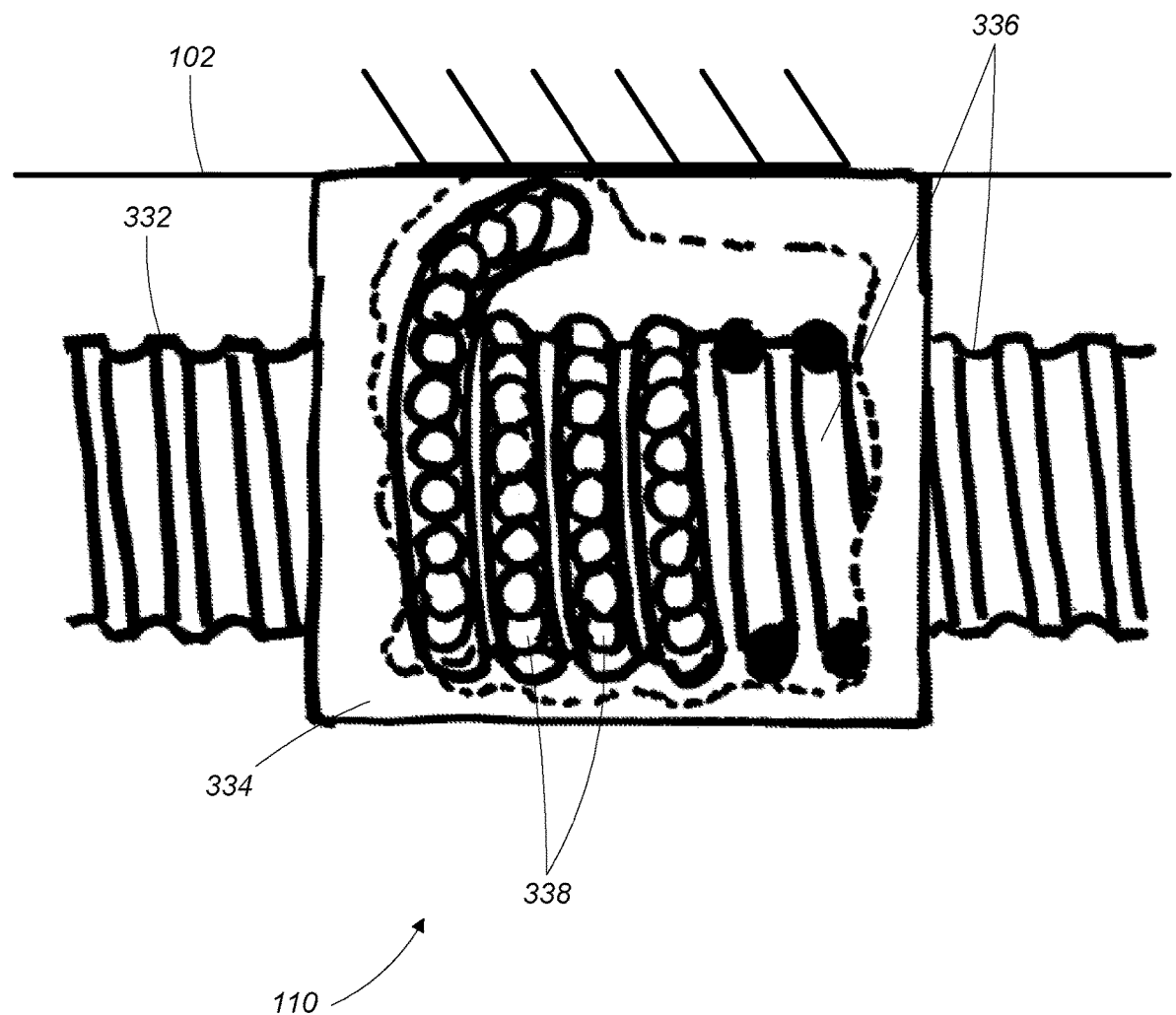
FIG. 2 is a cut-away diagram of a ball screw actuator.

Referring to FIG. 2, one example of a ball screw actuator 130 includes a screw 332 and a nut 334 (which is coupled to the housing in FIG. 1), each with matching helical grooves 336. A number of miniature balls 338 roll between the grooves 336, providing the only contact between the nut 334 and the screw 332. The nut 334 includes a return system (not shown) and a deflector (not shown) which, when the screw 332 or nut 334 rotates, deflects the miniature balls 338 into the return system. The balls 338 travel through the return system to the opposite end of the nut 334 in a continuous path. The balls 338 then exit from the ball return system into the grooves 336. In this way, the balls 338 continuously recirculate in a closed circuit as the screw 332 moves relative to the nut 334.

In some examples, the electromagnetic motor 126 is of a type selected from a variety of rotational electrical motors (e.g., a brushless DC motor). Electromagnetic motor 126 is configured to move the screw 332 of the ball screw actuator 130 back and forth along the longitudinal axis 122 by applying a torque (i.e., $\tau_M$) to either the screw 332 or the nut 334 of the ball screw actuator. The torque causes rotation of either the screw 332 or the nut 334, which in turn causes a force, $F_M(t)$, which is proportional to the torque applied by the motor, to be applied to the screw 332.

In some examples, the spring 128 is a helical coil type spring with a first end anchored to portion of the housing 102 and a second end anchored to the screw 332. In the configuration of FIG. 1, prior to actuation of the transdermal injection device 100, the spring 128 is in a stretched state in which it stores mechanical energy. Upon actuation, the spring 128 gradually releases its mechanical energy by compressing as it returns to a rest state. In some examples, the release of mechanical energy from the spring 128 results in application of a force, $F_S(t)=-kx$ (where k is the spring constant of the spring and x is the displacement of the spring from its rest position) to the screw 332 of the ball screw 130 in a direction along the longitudinal axis 122. The application of $F_S(t)$ to the screw 332 causes a corresponding application of a torque, $\tau_S$ to the screw 332 according to the following equation:

$$\tau_S = \frac{F_S P \eta}{2\pi}$$

where P is the lead of the screw 332, the lead being defined as an axial distance that the screw 332 advances through the nut 334 of the ball screw 130 over one complete turn (i.e., $2\pi$ radians) and $\eta$ is an efficiency of the ball screw 130 (i.e., a ratio of output work to input work).

In some examples, the combination of $F_M(t)$ and $F_S(t)$ is referred to as the input force that is provided to the linkage (e.g., the ball screw 130).

The application of the input force (i.e., the sum of $F_M(t)$ and $F_S(t)$) causes application of a net torque, $\tau_N$ to the screw 332. The net torque, $\tau_N$ is the sum of the torque applied to the screw 332 by the motor, $\tau_M$ and the torque applied to the screw 332 by the spring, $\tau_S$. The net torque applied to the screw 332, $\tau_N$ causes application of a net force, $F_N$ to the plunger 120 which in turn causes movement of the plunger 120 at a target velocity, $V_T$ along the longitudinal axis 122. The net force, $F_N$ is determined according to the following equation:

$$F_N = \frac{\tau_N 2\pi \eta}{P}$$

1.2 Control Loop

Referring again to FIG. 1, in some examples, the transdermal injection device 100 also includes a displacement sensor 140 and a controller 142. In general, the displacement sensor 140 measures a displacement, x(t) of the screw 332 of the ball screw actuator 130 and/or the plunger 120. In some examples, the displacement sensor 140 measures an incremental displacement of the screw 332 by storing an initial displacement value (i.e., x(0)) and monitoring a deviation from the starting value over time. In other examples, the displacement sensor 140 measures an absolute displacement of the screw 332.

The displacement, x(t) measured by the displacement sensor 140 is provided as input to the controller 142. As is described in greater detail below, the controller processes the displacement, x(t) to determine a motor control signal, y(t). The motor control signal, y(t) is provided to the motor 126 and which causes the motor torque, $\tau_M(t)$ to be applied to the screw 332, thereby causing movement of the screw 332 in a direction along the longitudinal axis 122.

1.3 System Diagram

Figure 3:
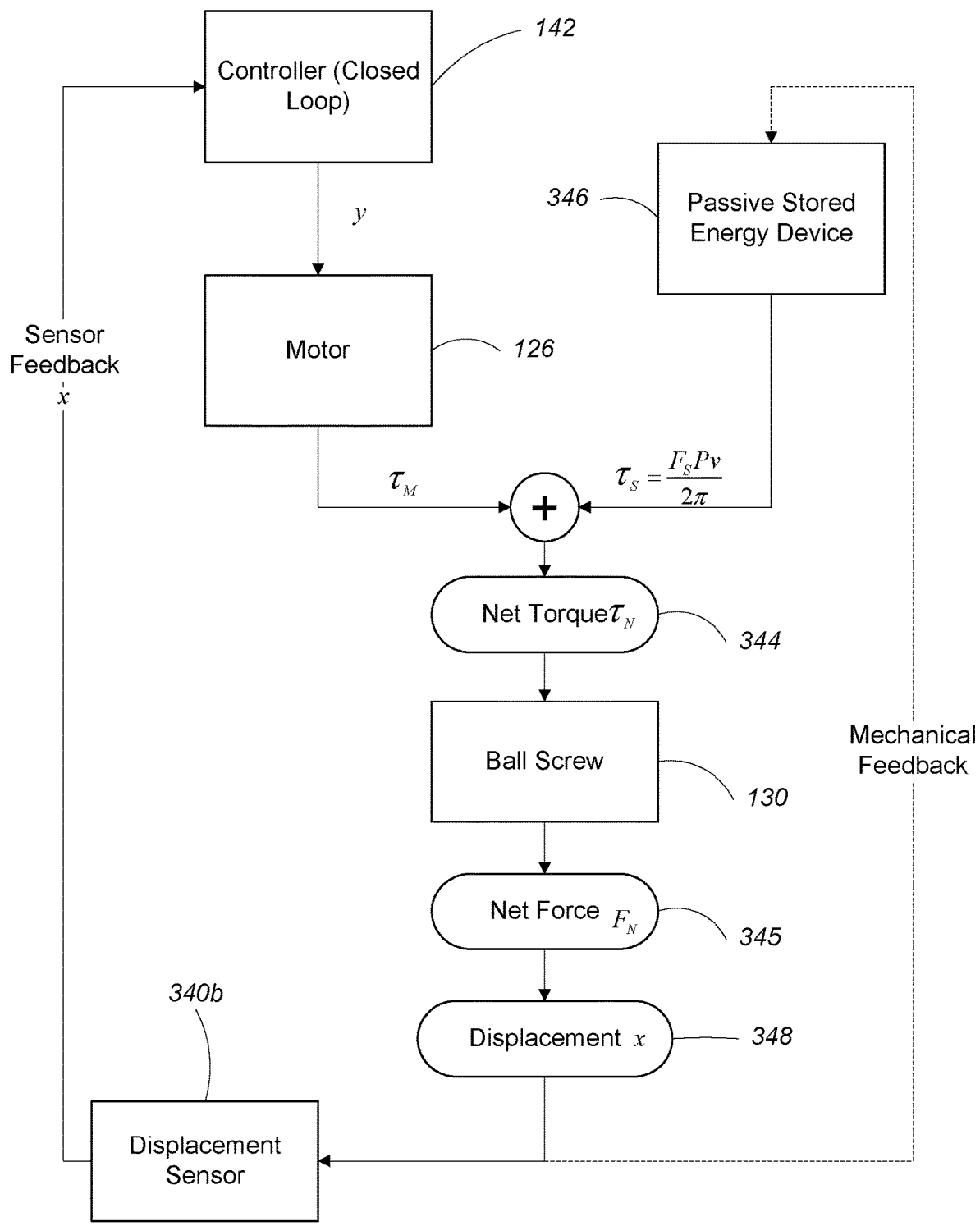
FIG. 3 is a block diagram of the controllable, needle-free transdermal injection device of FIG. 1.

Referring to FIG. 3, a schematic diagram of the system of FIG. 1 shows the net torque, $\tau_N$ 344 being applied to the ball screw 130. As is described above, the net torque, at a given time $t_1$, $\tau_N(t_1)$ 344 is a sum of a torque supplied by the controlled motor 126, at time $t_1$, $\tau_M(t_1)$ and a torque supplied by a passive stored energy device 346 (e.g., the spring 128 of FIG. 1) at time $t_1$, $\tau_S(t_1)$. Application of the net torque, $\tau_N(t_1)$ 344 to the ball screw 130 causes application of a net force, $F_N(t_1)$ 345 to the screw 332 of the ball screw 130 which in turn causes a displacement, $x(t_1)$ 348 of the screw 332.

The displacement, $x(t_1)$ 348 of the screw 332 of the ball screw 130 is measured by the displacement sensor 340 and is fed back to the controller 142. The displacement, $x(t_1)$ 348 of the screw 332 is also implicitly fed back to the passive stored energy device 346 as mechanical feedback since the stored energy device (e.g., the spring 128) applies a different amount of force (and associated torque) based on the displacement, $x(t_1)$ 348 of the screw 332 (e.g., according to Hooke's law).

As is described in greater detail below, the controller 142 processes the measured displacement, $x(t_1)$ 348 to determine a motor control signal, $y(t_1)$ which is supplied to the motor 126. The motor control signal, $y(t_1)$ causes the motor 126 to apply a torque, $\tau_M(t_2)$ to the screw 332 of the ball screw 130 at a time $t_2$ such that a sum of the torque applied by the motor, $\tau_M(t_2)$ and the torque applied by the passive stored energy device 346 at time $t_2$, $\tau_S(t_2)$ achieves a desired net torque, $\tau_N(t_2)$. As is noted above, the net torque applied to the screw 332, $\tau_N$ causes application of a net force, $F_N$ to the plunger 120 with the net force, $F_N$ being determined as:

$$F_N = \frac{\tau_N 2\pi \eta}{P}$$

Figure 4:
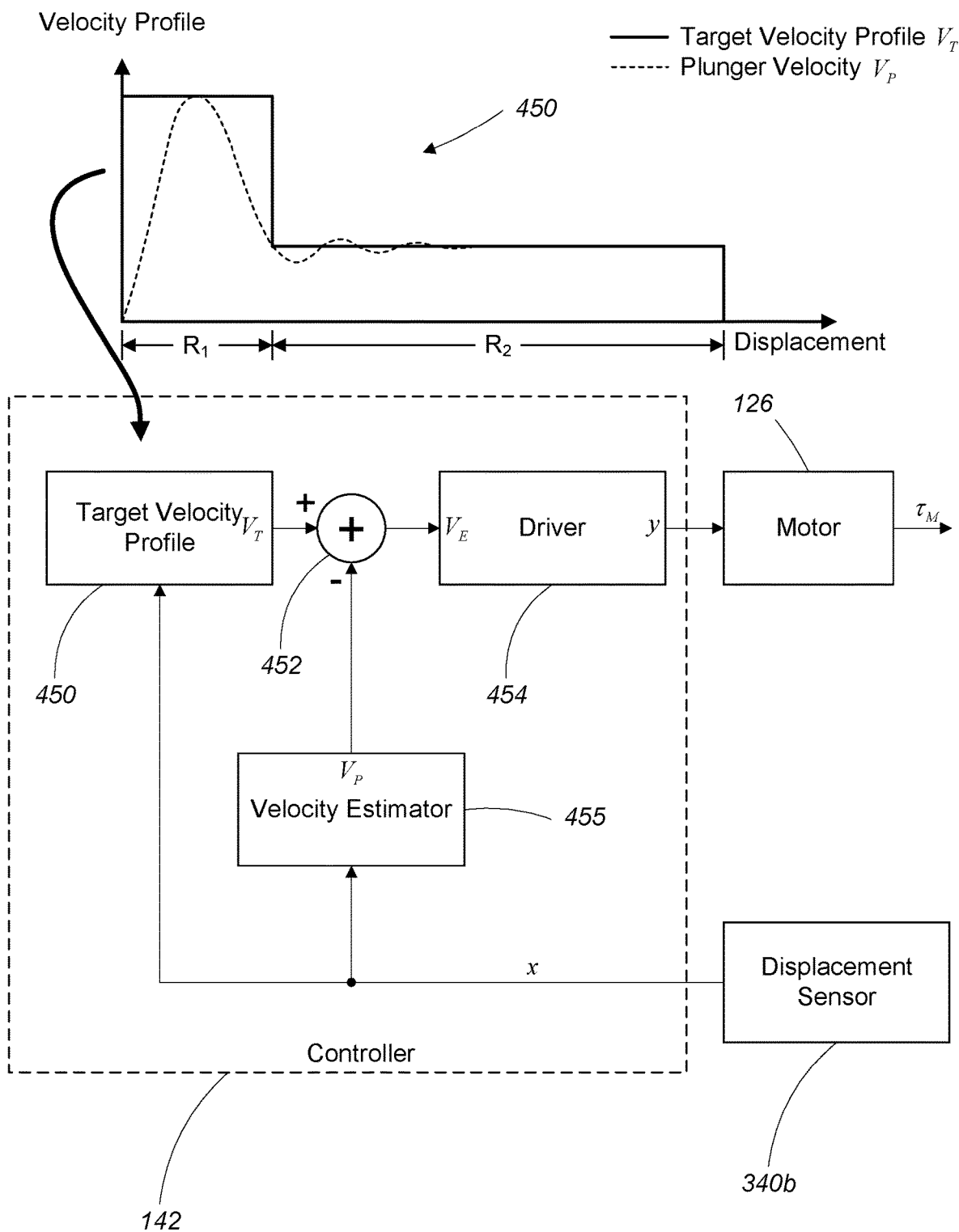
FIG. 4 is a block diagram of the controller of FIG. 2.

Referring to FIG. 4, in some examples the controller 142 includes a target velocity profile 450 which is proportional to a target force profile, a velocity estimator 455, a summing block 452, and a motor driver 454. Very generally, the controller 142 receives a displacement value, x from the displacement sensor 340 and provides the displacement value, x to both the force velocity profile 450 and the velocity estimator 455. The target velocity profile 450 processes the displacement value, x to determine a target plunger velocity value, $V_T$.

In some examples, the target velocity profile 450 includes a mapping between displacement values and target velocity values for an injection cycle or operational cycle (i.e., a range of time or distance over which the plunger 120 of the device moves). For example, the target velocity profile 450 shown in FIG. 4 has high target velocity values mapped to a range (i.e., $R_1$) of smaller displacement values and relatively lower target velocity values mapped to a range (i.e., $R_2$) of larger displacement values. In some examples, the target velocity profile 450 of FIG. 4 is used to provide an impulse of high velocity during an initial time period of an injection (e.g., to overcome an initial resistance of the skin) and to provide a substantially lower constant velocity for a remaining time period of the injection (e.g., to deliver the injectate through the skin). Note that, since changes in velocity are not instantaneous, the actual velocity profile of the plunger 120, $V_P$ does not exactly track the ideal target velocity profile, $V_T$.

The velocity estimator 455 processes the displacement value, x to determine an estimate of a plunger velocity, $V_P$. In general, the velocity estimator 455 determines the estimate of the plunger velocity, $V_P$ a value read from an encoder (e.g., a linear absolute encoder or an incremental rotary encoder on, for example, the motor or on a nut of the ball screw).

The target plunger velocity, $V_T$ is provided to the summing block 452 along with the estimate of the plunger velocity, $V_P$ from the velocity estimator 455. The summing block 452 subtracts the estimate of the plunger velocity, $V_P$ from the target plunger velocity, $V_T$ to obtain an error signal, $V_E$. The error signal, $V_E$ is provided to the motor driver 454 which converts the error signal to a motor control signal, y for driving the motor 126.

In operation, the controller 142 of FIG. 4 uses a feedback control approach to ensure that a combination of the controlled torque applied to the screw 332 of the ball screw 130 due to the motor 126, $\tau_M$ and the torque, $\tau_S$ applied to the screw 332 of the ball screw 130 due to the passive stored energy device 342 (e.g., the spring) causes the velocity of the plunger, $V_P$ to track the target velocity profile 450 as the screw 332 is displaced. That is, the motor 126 is controlled to apply a torque on the screw 332 that either supplements or counteracts the torque applied to the screw 332 by the passive stored energy device 342 to achieve the target plunger velocity, $V_T$ for a given displacement of the screw 332.

2 Target Velocity Profiles

Figure 5:
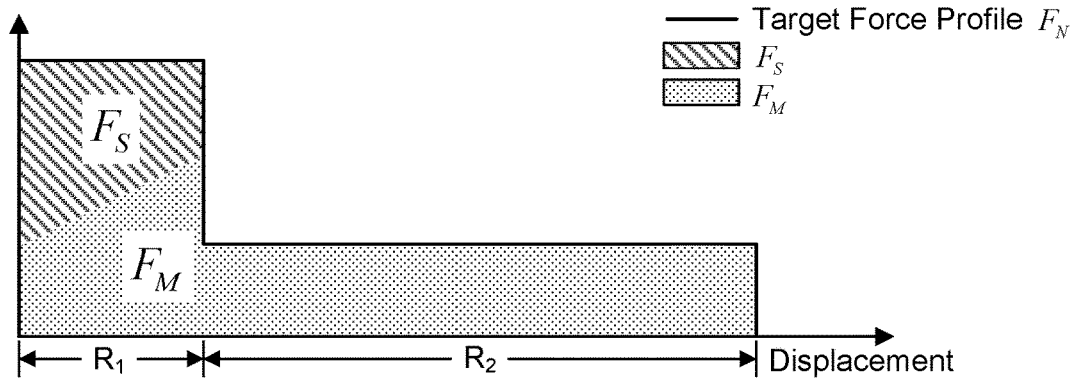
FIG. 5 shows one example of the combined force contributions of a spring and a motor achieving a first target force profile.
Figure 6:
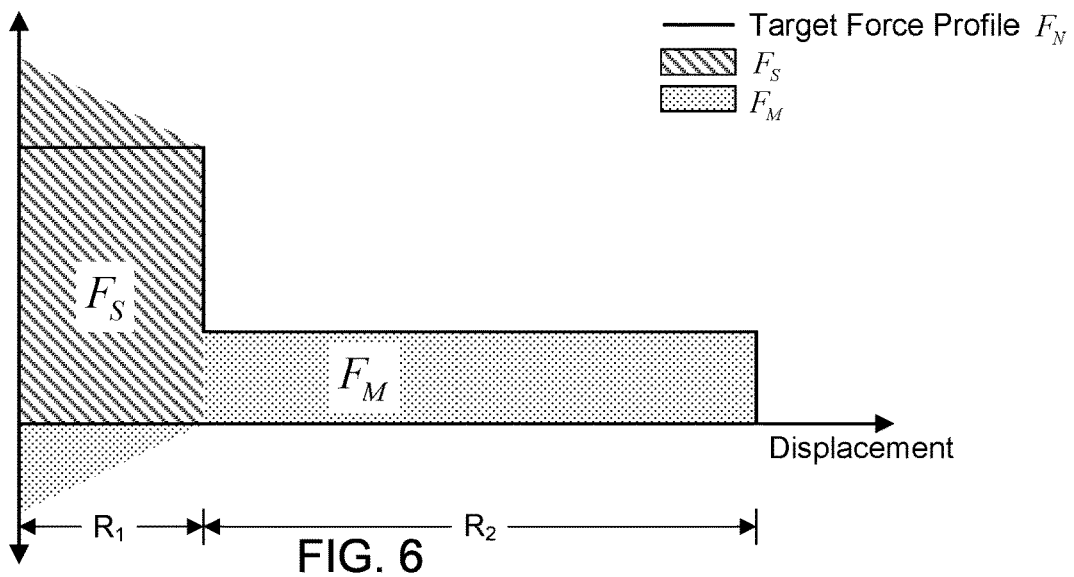
FIG. 6 shows another example of the combined force contributions of a spring and a motor achieving the first target force profile.
Figure 7:
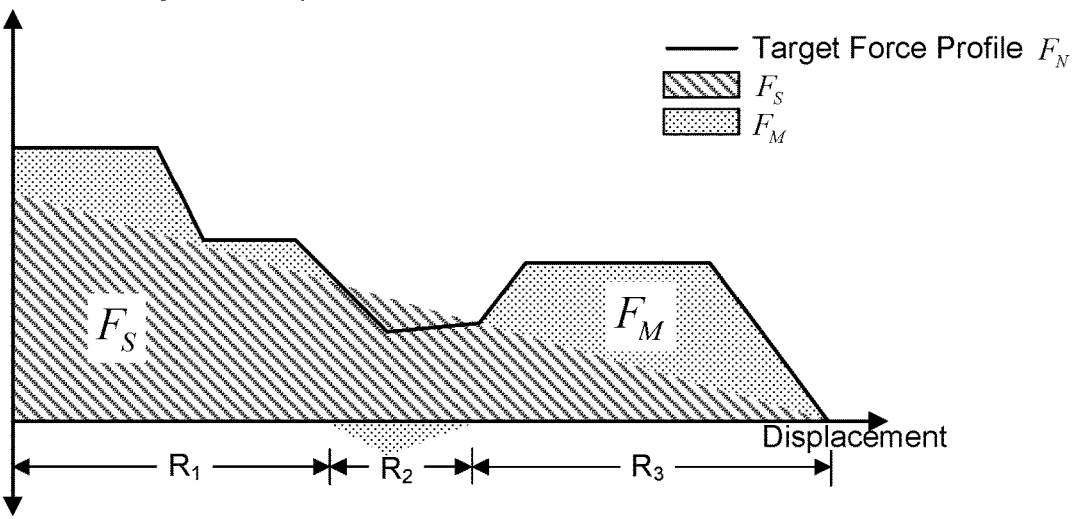
FIG. 7 shows another example of the combined force contributions of a spring and a motor achieving a second target force profile.

Referring to FIG. 5-FIG. 7, three exemplary target force profiles illustrate the respective force components from the motor 126 (i.e., $F_M$) and the spring 128 (i.e., $F_S$) that achieve a target net force (i.e., $F_T$) which is proportional to a target velocity (i.e., $V_T$) of the plunger 120. While the target profiles of FIG. 5-FIG. 7 are shown as target force profiles to facilitate a clear explanation, it is noted that in the devices described herein, the target profile may be represented as a velocity profile (as in FIG. 4).

Referring to FIG. 5, in one example, a target force profile 550 has relatively high target net force values mapped to a first range (i.e., $R_1$) of smaller displacement values and relatively lower target net force values mapped to a second range (i.e., $R_2$) of larger displacement values. In the target force profile 550 of FIG. 5, at the very beginning of the first range when the injection begins, the force, $F_S$ exerted on the screw 332 by the passive stored energy device 342 is at a maximum but is not great enough to achieve the target net force, $F_T$ for the initial displacement of the screw 332. Thus, the controller 142 controls the motor 126 to exert a supplementary force, $F_M$ equal to the difference between the target net force, $F_T$ and the force, $F_S$ exerted on the screw 332 by the passive stored energy device 342.

As the displacement of the screw 332 increases over the first range, the amount of force exerted on the screw 332 by the passive stored energy device 342 decreases at first rate (i.e., according to Hooke's law). To maintain the target net force, $F_T$ exerted on the screw 332 (and the target velocity, $V_T$) as the amount of force exerted on the screw 332 by the passive stored energy device 342 decreases, the controller 142 controls the motor 126 to increase the supplementary force, $F_M$ exerted on the screw 332 by the motor 126 at the first rate.

After the displacement of the screw 332 passes the end of the first range and moves into the second range where the passive stored energy device 342, before reaching its rest position, stops exerting force on the screw 332. For example, a range of motion of the passive stored energy device 342 (e.g., a range of expansion or contraction of a spring) may be mechanically limited by a stopping member (not shown) such that the passive stored energy device 342 disengages from or otherwise no longer exerts a force on the screw 332 before the passive stored energy device 342 reaches a rest position. In operation, prior to reaching the end of its limited range of motion, the passive stored energy device 342 engages and exerts a force on the screw 332 (e.g., a spring pushes on an end of the screw 332). Once the passive stored energy device 342 reaches the stopping member it disengages from and stops exerting force on the screw 332. With the passive stored energy device 342 disengaged from the screw 332, the controller 142 controls the motor 126 to maintain a relatively constant target force, $F_T$ (and target velocity, $V_T$) as the screw 332 moves through the second range.

In some examples, the target profile of FIG. 5 is used when high acceleration of the plunger is a driving design factor.

Referring to FIG. 6, in another example, a target force profile 650 similar to that described above in FIG. 4 and FIG. 5 has relatively high target net force values mapped to a first range (i.e., $R_1$) of smaller displacement values and relatively lower target net force values mapped to a second range (i.e., $R_2$) of larger displacement values. At the very beginning of the first range, when the injection begins, the force, $F_S$ exerted on the screw 332 by the passive stored energy device 342 is at a maximum and exceeds the target force, $F_T$ (and therefore the target velocity, $V_T$) for the initial displacement of the screw 332. Thus, the controller 142 controls the motor 126 to exert a counteracting force, $F_M$ equal to the difference between the target net force, $F_T$ and the force, $F_S$ exerted on the screw 332 by the passive stored energy device 342.

As the displacement of the screw 332 increases over the first range, the amount of force exerted on the screw 332 by the passive stored energy device 342 decreases at first rate (i.e., according to Hooke's law). To maintain the target net force, $F_T$ exerted on the screw 332 (and the target velocity, $V_T$) as the amount of force exerted on the screw 332 by the passive stored energy device 342 decreases, the controller 142 controls the motor 126 to decrease the counteracting force, $F_M$ exerted on the screw 332 by the motor 126 at the first rate. In this way, the excess of force exerted on the screw 332 by the passive stored energy device 342 is counteracted by the motor 126.

After the displacement of the screw 332 passes the end of the first range and moves into the second range, the passive stored energy device 342 is disengaged from the screw 332 before reaching its rest position and therefore stops exerting force on the screw 332. The controller 142 controls the motor 126 to maintain a relatively constant target force, $F_T$ (and target velocity, $V_T$) as the screw 332 moves through the second range.

In some examples, the target profile of FIG. 6 is used when minimizing the size of the motor and the demand on the electromechanical components of the needle-free transdermal injection device is a driving design factor.

Referring to FIG. 7, in another example, a target force profile 750 has an irregular shape. In this case, the passive stored energy device 342 exerts a force on the screw 332 over an entire displacement of the screw 332 and is the primary source of force exerted on the screw. The motor 126 is used to slightly augment and counteract the force exerted by the passive stored energy device 342.

In a first range (i.e., $R_1$) of displacement values and in a third range (i.e., $R_3$) of displacement values, the force exerted on the screw 332 by the passive stored energy device 342 is not great enough to achieve the target net force, $F_T$ (or the target velocity, $V_T$) for the displacement values in the ranges. Thus, in the first range and in the third range, the controller 142 controls the motor 126 to exert a supplementary force, $F_M$ equal to the difference between the target net force, $F_T$ and the force, $F_S$ exerted on the screw by the passive stored energy device 342.

In a second range (i.e., $R_2$) of displacement values, the force $F_S$ exerted on the screw 332 by the passive stored energy device 342 exceeds the target net force values, $F_T$ for the displacements in the range. Thus, in the third range, the controller 142 controls the motor 126 such that it exerts a counteracting force, $F_M$ to the screw 332 that is equal and opposite to the excess force exerted on the screw 332 by the passive stored energy device 342.

One advantage of using a target profile such as that shown in FIG. 7 is that, by using the passive stored energy device 342 as a primary force generator, the size, cost, and power requirements of the motor 126 can be reduced.

It is noted that the target force profiles of FIGS. 5-7 are just a few examples of target force profiles that can be used to achieve target velocity profiles, and a virtually infinite number of target force profiles may be used, depending on the specific application of the needle-free transdermal injection device. In some examples, the target force profile is limited based on the maximum forces that can be supplied by the motor and the passive stored energy device.

In general, design of the needle-free transdermal injection device can be optimized for a given application by choosing the respective weights, sizes, and costs of the active force generation device (e.g., the motor) and the passive force generation device (e.g., the spring) such that both an optimality criterion (e.g., low power operation) and the a target force profile are achieved. For example, to achieve a low power operation optimality criterion, a spring can be used to supplement the force generated by a relatively smaller motor.

3 Alternative Needle-Free Transdermal Injection Device Configurations

Figure 8:
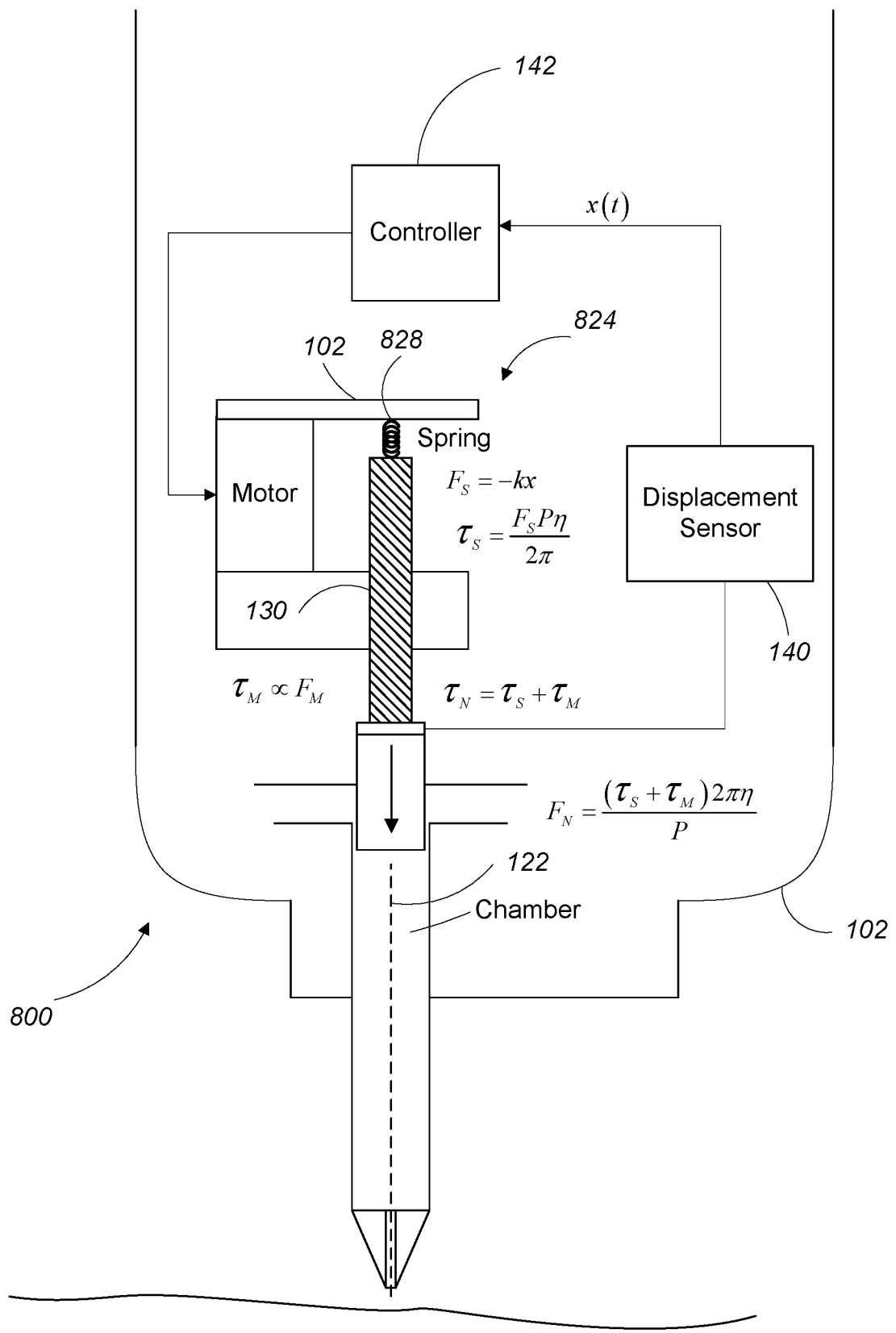
FIG. 8 is a schematic diagram of an alternative configuration of a controllable, needle-free transdermal injection device.

Referring to FIG. 8, a controllable, needle-free transdermal injection device 800 includes an alternative force generating mechanism 824. The alternative mechanism 824 includes a spring 828 (e.g., a helical coil type spring) with a first end anchored to portion of the housing 102 and a second end anchored to the screw 332 of the ball screw 130. Prior to actuation of the transdermal injection device 800, the spring 828 is in a compressed state in which it stores mechanical energy. Upon actuation, the spring 828 gradually releases its mechanical energy by decompressing as it returns to a rest state. In some examples, the release of mechanical energy from the spring 828 results in application of a force, $F_S(t)=-kx$ to the screw 332 of the ball screw 130 in a direction along the longitudinal axis 122. As was the case in previous examples, the application of $F_S(t)$ to the screw 332 causes application of a torque, $\tau_S$ to the screw 332 according to the following equation:

$$\tau_S = \frac{F_S P \eta}{2\pi}$$

where P is the lead of the screw 332, the lead being defined as an axial distance that the screw 332 advances through the nut 334 of the ball screw 130 over one complete turn (i.e., $2\pi$ radians) and $\eta$ is an efficiency of the ball screw 130 (i.e., a ratio of output work to input work).

A net torque, $\tau_N$ applied to the screw 332 is the sum of the torque applied to the screw 332 by the motor, $\tau_M$ and the torque applied to the screw 332 by the spring, $\tau_S$. The net torque applied to the screw 332, $\tau_N$ causes application of a net force, $F_N$ to the plunger 120. The net force, $F_N$ is determined according to the following equation:

$$F_N = \frac{\tau_N 2\pi \eta}{P}$$

As was the case in previous examples, the controller 142 controls the motor 126 to apply a torque on the screw 332 that either supplements or counteracts the torque applied to the screw 332 by the passive stored energy device 828 to achieve a target net force, $F_T$ and a corresponding target plunger velocity, $V_T$ for a given displacement of the screw 332.

Figure 9:
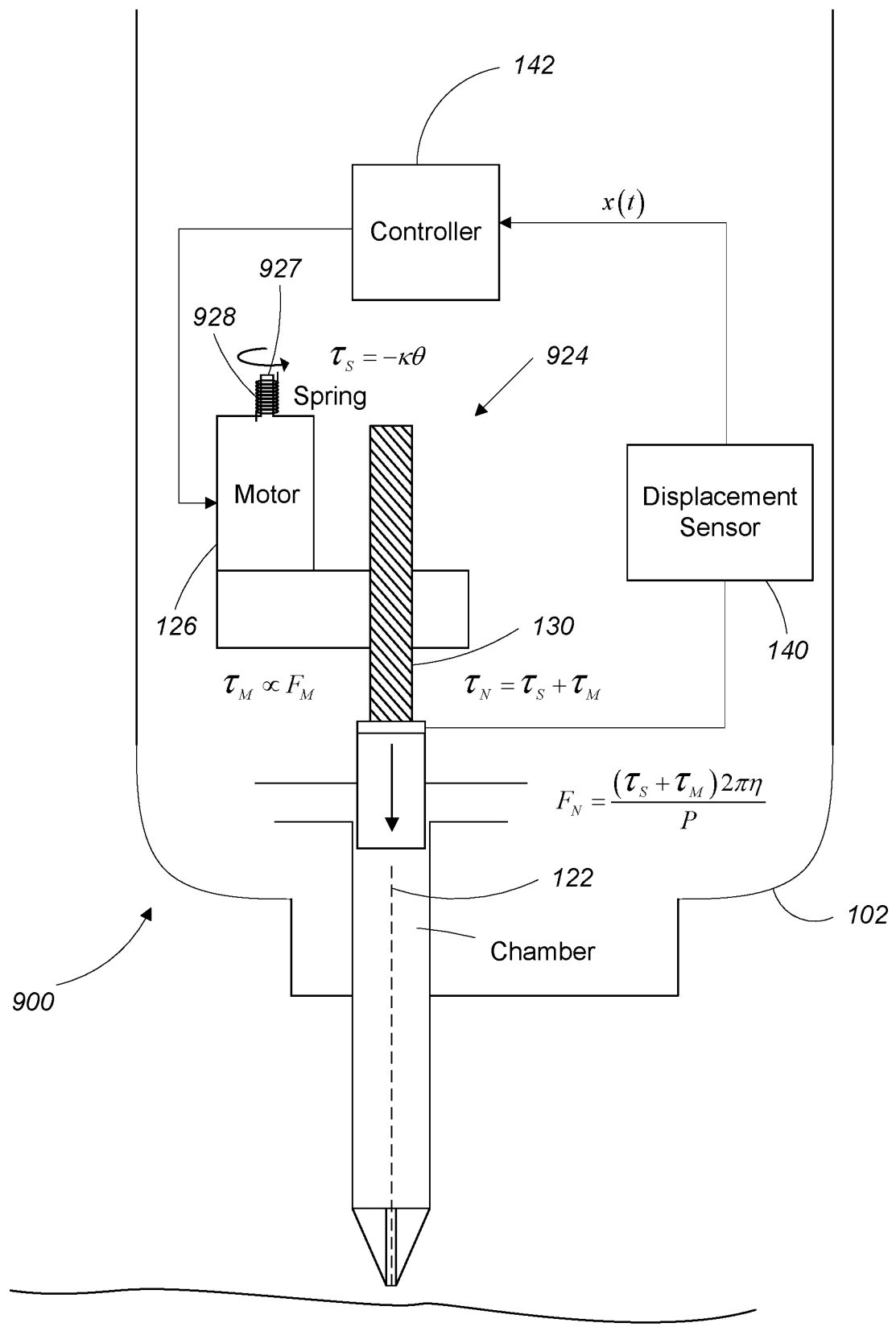
FIG. 9 is a schematic diagram of another alternative configuration of a controllable, needle-free transdermal injection device.

Referring to FIG. 9, a controllable, needle-free transdermal injection device 900 includes another alternative force generating mechanism 924. The alternative force generating mechanism 924 includes a helical coil torsion spring 928 with a first end anchored to a body of the motor 126 and a second end anchored to a shaft 927 of the motor 126. Prior to actuation of the transdermal injection device 900, the spring 928 is in a twisted state in which it stores mechanical energy. Upon actuation, the spring 928 gradually releases its stored mechanical energy by un-twisting as it returns to a rest state. In some examples, as the spring 928 un-twists, the shaft 927 of the motor 126 rotates, thereby causing application of a torque, $\tau_S(t)=-k\theta$ (where k is the spring's torsion coefficient and $\theta$ is the angle of twist from the spring's rest position), via the motor 126, to the screw 332 of the ball screw 130. A net torque, $\tau_N$ applied to the screw 332 is the sum of the torque applied directly to the screw 332 by the motor, $\tau_M$ and the torque applied to the screw 332 via the motor 126 by the spring, $\tau_S$. The net torque applied to the screw 332, $\tau_N$ causes application of a net force, $F_N$ to the plunger 120. The net force, $F_N$ is determined according to the following equation:

$$F_N = \frac{\tau_N 2\pi \eta}{P}$$

As was the case in previous examples, the controller 142 controls the motor 126 to apply a torque on the screw 332 that either supplements or counteracts the torque applied to the screw 332, via the motor 126, by the passive stored energy device 928 to achieve a target net force, $F_T$ and a corresponding target plunger velocity, $V_T$ for a given displacement of the screw 332.

Figure 10:
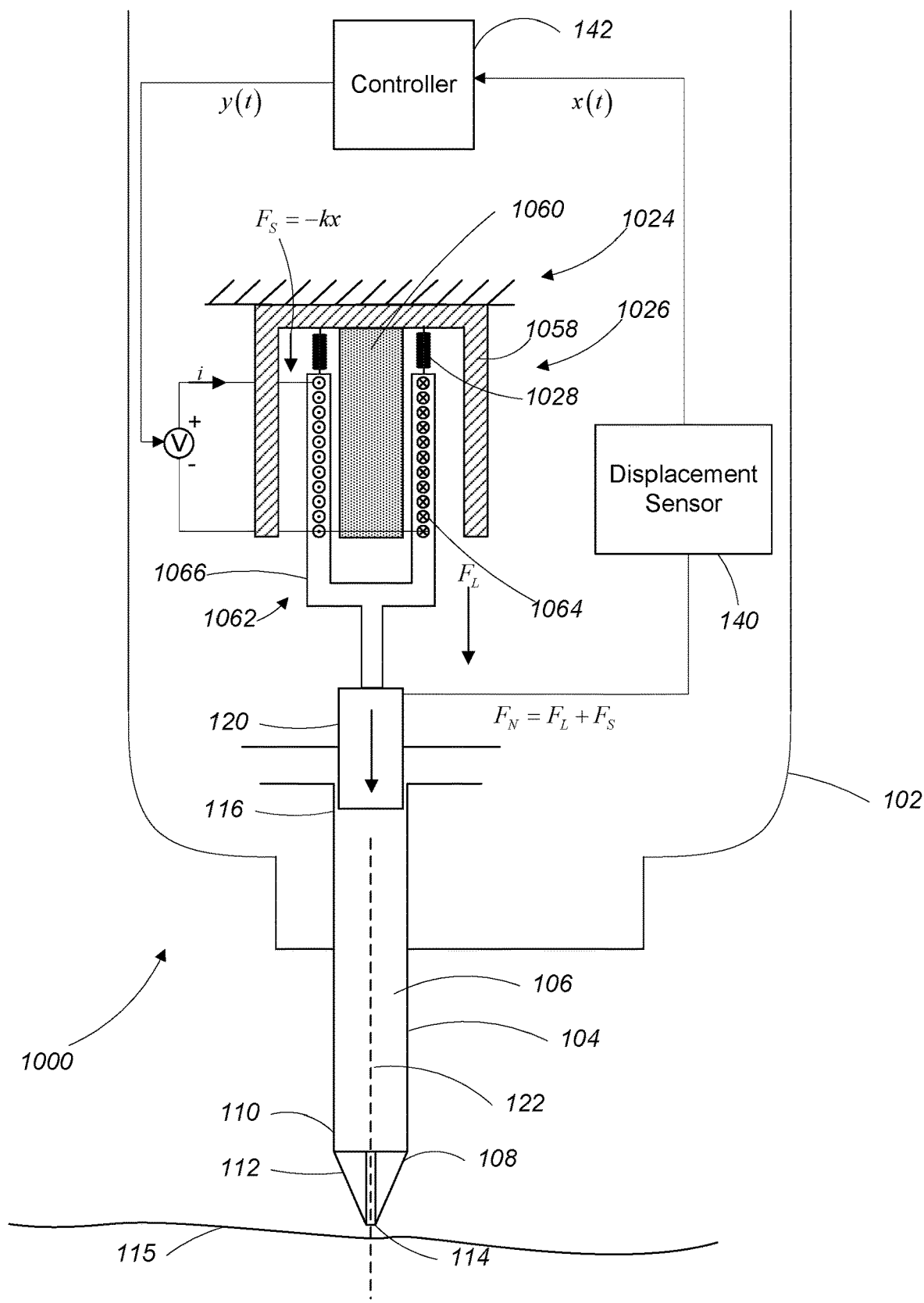
FIG. 10 is a schematic diagram of another alternative configuration of a controllable, needle-free transdermal injection device.

Referring to FIG. 10, another example of a controllable, needle-free transdermal injection device 1000 includes an alternative force generating mechanism 1024. The alternative force generating mechanism 1024 includes a linear electrical motor 1026 (in this case a Lorentz force linear electrical motor) and one or more helical springs 1028.

In some examples, the linear electrical motor 1026 includes a metallic sheath 1058 coupled to the housing 102. A magnet 1060 is disposed within and attached to the metallic sheath 1058. The motor 1026 also includes a coil assembly 1062 disposed within the metallic sheath 1058, surrounding the magnet 1060, and coupled to the plunger 120. The coil assembly 1062 includes a coil 1064 and a coil housing 1066. The coil assembly 1062 is movable along a longitudinal axis 122 of the device 1000 by applying a voltage to the coil 1064 (wherein a polarity of the voltage controls a direction movement of the coil assembly 1062). Movement of the coil assembly 1062 due to the voltage applied to the coil 1064 causes application of a force, $F_M(t)$ to the plunger 120 in a direction along the longitudinal axis 122.

The one or more springs 1028 each have a first end anchored to the coil assembly 1062 and a second end anchored to the housing 102 (e.g., via the metallic sheath 1058). Prior to actuation of the transdermal injection device 1000, the springs 1028 are in a compressed state in which they store mechanical energy. Upon actuation, the springs 1028 gradually release their mechanical energy by decompressing as they return to a rest state. In some examples, the release of mechanical energy from the springs 1028 results in application of a force, $F_S(t)$ to the plunger 120 (via the coil assembly 1062) in a direction along the longitudinal axis 122. A net force applied, $F_N(t)$ applied to the plunger 120 is the sum of the force applied by the springs 1028, $F_S(t)$ and the force applied by the motor 1028, $F_M(t)$.

In general, the controller 142 controls the voltage applied to the coil 1064 to either supplement or counteract the force applied to the coil assembly 1062 by the spring(s) 1028 to achieve a target net force, $F_T$ and a corresponding a target plunger velocity, $V_T$ for a given displacement of the plunger 120.

Figure 11:
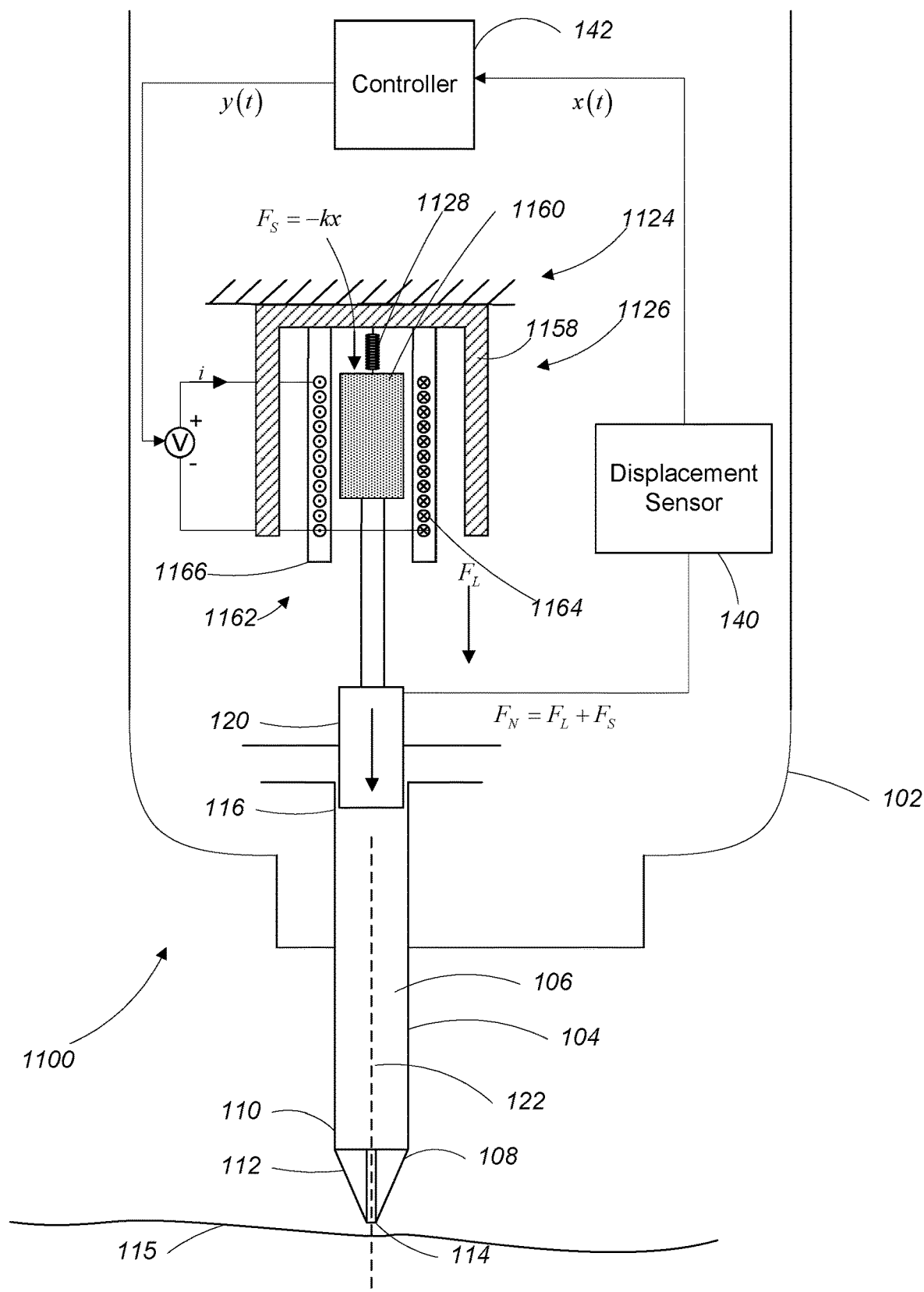
FIG. 11 is a schematic diagram of another alternative configuration of a controllable, needle-free transdermal injection device.

Referring to FIG. 11, another example of a controllable, needle-free transdermal injection device 1100 includes an alternative force generating mechanism 1124. The alternative force generating mechanism 1124 includes a linear electrical motor 1126 (in this case a Lorentz force linear electrical motor) and one or more helical springs 1128.

In some examples, the linear electrical motor 1126 includes a metallic sheath 1158 coupled to the housing 102. A coil assembly 1162 is coupled to the housing 102 either via the metallic sheath 1158 (as is shown in FIG. 11) or directly. The coil assembly 1162 includes a coil 1164 and a coil housing 1166. A magnet 1160, which is disposed within the coil assembly 1162, is coupled to both the housing 102 (e.g., via the spring 1128) and the plunger 120. The magnet 1160 is movable along a longitudinal axis 122 of the device 1100 by applying a voltage to the coil 1164 (wherein a polarity of the voltage controls a direction movement of the magnet 1160). Movement of the magnet 1160 due to the voltage applied to the coil 1164 causes application of a force, $F_M(t)$ to the plunger 120 in a direction along the longitudinal axis 122.

The spring 1128 has a first end anchored to the magnet 1160 and a second end anchored (either directly or via the metallic sheath 1158) to the housing 102. Prior to actuation of the transdermal injection device 1100, the spring 1128 is in a compressed state in which it stores mechanical energy. Upon actuation, the spring 1128 gradually releases its mechanical energy by decompressing as it returns to a rest state. In some examples, the release of mechanical energy from the spring 1128 results in application of a force, $F_S(t)$ to the plunger 120 (via the magnet 1160) in a direction along the longitudinal axis 122. A net force applied, $F_N(t)$ applied to the plunger 120 is the sum of the force applied by the spring 1128, $F_S(t)$ and the force applied by the motor 1126, $F_M(t)$.

In general, the controller 142 controls the voltage applied to the coil 1164 to either supplement or counteract the force applied to the magnet 1160 by the spring(s) 1128 to achieve a target net force, $F_T$ and a corresponding a target plunger velocity, $V_T$ for a given displacement of the plunger 120.

4 Reusable Needle-Free Transdermal Injection Device

In some examples, the needle-free transdermal injection device is reusable. In such examples, after performing an injection, the passive stored energy device has released some or all of its stored energy and needs to be reset (e.g., re-compressed, re-stretched, or re-twisted). A number of different techniques can be used to apply mechanical, manual, or electrical energy to reset to passive stored energy device.

In some examples, the motor of the needle-free transdermal injection device is used to reset the passive stored energy device. That is, the motor can be engaged with the passive stored energy device and can then generate torque (and a corresponding force) which is used to reset the passive stored energy device. Even in cases where the motor is not particularly powerful, the motor can be used over a relatively long duration of time to reset the passive stored energy device. In some examples, the needle-free transdermal injection device includes one or more electrical energy storage elements (e.g., capacitors or batteries) for storing electrical energy. The electrical energy stored in the electrical energy storage elements can be used for both the injection cycle (sometimes referred to as an operational cycle) and to reset the passive stored energy device (e.g., by powering the motor). In some examples, when the device is plugged into an electrical socket (e.g., a wall socket), the electrical energy storage elements can be charged and used to reset the passive stored energy device.

In some examples, rather than using the motor in the needle-free transdermal injection device to reset the passive stored energy device, a base station is provided for resetting the passive stored energy device. In some examples, the base station receives line power and includes a larger, more powerful motor for resetting the (potentially larger) passive energy stored energy device. The base station may be configured to receive the needle-free transdermal injection device such that the larger, more powerful motor included in the base station engages the passive stored energy device. Once the motor of the base station is engaged with the passive stored energy device, the motor of the base station can be used to quickly reset the passive stored energy device. In some examples, the base station automatically resets the passive stored energy device once the motor of the base station is engaged with the passive stored energy device. In some examples, an operator must actuate the base station (e.g., by pressing a button) to initiate resetting of the passive stored energy device by the base station.

In some examples, a manually operated device (e.g., a manually operated base station) is used to reset the passive stored energy device. For example, a manually operated base station may be configured to receive the needle-free transdermal injection device such that the passive stored energy device engages a manual resetting mechanism of the manually operated base station. An operator can then manually reset the passive stored energy device by manually actuating the manual resetting mechanism by, for example, opening and closing a lid of the manually operated base station.

5 Alternatives

In some examples, stored energy devices other than springs can be used for the passive stored energy device. For example, compressed gas or elastic materials (e.g., rubber bands) may be used to store and release mechanical energy. In some examples flexures (e.g., beam springs) such as C-shaped carbon fiber members are used. For example, the device may include multiple (e.g., two) beam springs arranged on two or more sides of the device and configured to apply force to the ball screw (or another suitable force transfer device). In some examples, a gas spring or gas piston may be used as the passive stored energy device. In such examples, the entire could be pressurized and the pressure in the chamber can be used to pressurize the gas spring.

In some examples, magnets may be used as the passive stored energy device. For example, a positive pole of a magnet coupled to the ball screw can be held in proximity of a positive pole of a magnet coupled to the housing, thereby storing mechanical energy. Upon actuation, the magnet coupled to the ball screw can be released and allowed to move away from the magnet coupled to the housing (due to the repulsive force between the two magnets), thereby applying a force to the ball screw.

In some examples, only a portion of a range of operation of a spring is used (e.g., a portion of the range of operation where the spring operates linearly). For example, a spring may be able to apply force in a range of 0 N to 300 N, but may only operate linearly in the 200 N to 300 N range. Thus, the 200 N to 300 N range may be used by the needle-free transdermal injection device.

In some examples, only one of the displacement and the net force is measured and fed back to the controller. For example, based on empirically derived data, there may be a pre-determined lookup table or mapping function that maps displacement values to corresponding motor control signals, y.

In examples where empirically determined data is used to eliminate the need for one or more measurements of net force or displacement, there may be multiple sets of empirically determined data based on, for example, injection location. For example, one set of empirically determined data may be used when injecting into a patient's arm and another, different set of empirically determined data may be used when injecting into a patient's buttock.

While the above examples describe a closed loop feedback control based approach, in some examples, open loop control may be used. For example, based on empirically derived data, it may be possible to pre-determine a time-based velocity profile for the motor. Then without feeding back any information related to force or displacement, the motor can adjust the motor control signal over the course of an injection.

In some examples, if the passive stored energy device is capable of providing sufficient force for the entire injection process, the controllable, needle-free transdermal injection device may entirely omit using a motor. For example, a controllable braking system could be used to counteract the force exerted by the passive stored energy device to achieve a target velocity profile.

In some examples where a ball screw is used, either the screw or the nut of the ball screw is coupled to the housing. In the case that the screw is coupled to the housing, the nut is able to move along the screw. In the case that the nut is coupled to the housing, the screw is able to move back and forth through the nut.

It is noted that the term 'cartridge' as used throughout this specification is not intended to limit the application to any particular container or device for holding injectate. In the context of this specification, the term cartridge should be understood as pertaining to any container for holding and allowing extraction of fluids such as medicaments. It is to be understood that the foregoing description is intended to illustrate and not to limit the scope of the invention, which is defined by the scope of the appended claims. Other embodiments are within the scope of the following claims.

What is claimed is:

1. An apparatus for use in injectate delivery, the apparatus comprising:
    an actuator including a linkage, a force generating mechanism mechanically coupled to the linkage, and a controller coupled to the force generating mechanism;
    wherein the force generating mechanism includes a passive force generator and an active force generator, the active force generator comprising an actively controlled force generating device, the passive force generator comprising a spring storing mechanical energy and configured to release the mechanical energy upon actuation as a first force on the linkage, and the actively controlled force generating device comprising at least one electromagnetic motor configured to apply a second force to the linkage in response to a control signal from the controller, wherein the first force released by the passive force generator supplements the second force from the actively controlled force generating device, resulting in a net force on the linkage that is a sum of the first force and the second force when driving the linkage during injectate delivery; and
    wherein the controller is configured, in a reset mode, to control the at least one electromagnetic motor to apply a resetting force to the linkage to compress the spring such that mechanical energy is stored in the spring, and in an injection mode, to control the at least one electromagnetic motor, upon actuation, to maintain a net force upon the linkage by varying the second force from the at least one electromagnetic motor during application of the first force by the spring such that the net force drives a velocity of the linkage toward a target velocity.

2. The apparatus of claim 1 wherein the controller is configured to control an input force provided to the linkage, including controlling the second force to cause movement of the actuator at a target velocity.

3. The apparatus of claim 2 wherein the controller is configured to indirectly control the second force provided by the active force generator by controlling a torque generated by the active force generator, wherein the torque is proportional to the second force.

4. The apparatus of claim 2 wherein the controller is further configured to control the input force provided to the linkage such that velocity of the actuator achieves a target velocity profile over an operational cycle of the apparatus.

5. The apparatus of claim 2 further comprising a displacement sensor for measuring a displacement of the actuator from a reference position, wherein the controller includes an input for receiving a displacement measurement of the actuator from the displacement sensor and is configured to determine an estimate of a velocity of the actuator based on the received displacement measurement.

6. The apparatus of claim 5 wherein the controller is configured to determine the estimate of the velocity of the actuator based on the received displacement measurement and one or more previously received displacement measurements.

7. The apparatus of claim 1, wherein the electromagnetic motor includes an electromagnetic rotary motor.

8. The apparatus of claim 1, wherein the electromagnetic motor includes an electromagnetic linear motor.

9. The apparatus of claim 8 wherein the spring comprises a torsion spring directly coupled to the motor.

10. The apparatus of claim 8 wherein the spring comprises a torsion spring directly coupled to the linkage.

11. The apparatus of claim 8 wherein the spring comprises a beam spring.

12. The apparatus of claim 1 wherein the spring comprises a helical spring directly coupled to the linkage.

13. The apparatus of claim 12 wherein the helical spring is configurable into a rest state wherein the helical spring stores no mechanical energy and into a compressed state wherein the helical spring stores mechanical energy.

14. The apparatus of claim 12 wherein the helical spring is configurable into a rest state wherein the helical spring stores no mechanical energy and into an expanded state wherein the helical spring stores mechanical energy.

15. The apparatus of claim 1 further comprising a chamber for holding an injectate, wherein the actuator is disposed within the chamber and is configured to exert a net force, proportional to the input force on the injectate in the chamber via the linkage during operation.

16. The apparatus of claim 1 wherein the linkage comprises a ball screw.

* * * * *